(12) United States Patent
Nissilä

(10) Patent No.: US 7,742,808 B2
(45) Date of Patent: Jun. 22, 2010

(54) HEART RATE MONITOR, METHOD AND COMPUTER SOFTWARE PRODUCT

(75) Inventor: Seppo Nissilä, Oulu (FI)

(73) Assignee: Polar Electro Oy, Kempele (FI)

( * ) Notice: Subject to any disclaimer, the term of this patent is extended or adjusted under 35 U.S.C. 154(b) by 1013 days.

(21) Appl. No.: 11/244,447

(22) Filed: Oct. 5, 2005

(65) Prior Publication Data
US 2006/0094969 A1    May 4, 2006

(30) Foreign Application Priority Data
Oct. 15, 2004    (FI)    ................................ 20045392

(51) Int. Cl.
*A61B 5/0402* (2006.01)
(52) U.S. Cl. ...................................... 600/513
(58) Field of Classification Search ................ 600/509, 600/513, 520, 561; 607/60
See application file for complete search history.

(56) References Cited

U.S. PATENT DOCUMENTS

| | | | |
|---|---|---|---|
| 5,840,039 A | 11/1998 | Heikkila | |
| 6,461,312 B1 | 10/2002 | Ganshorn | |
| 6,798,378 B1 | 9/2004 | Walters | |
| 7,273,457 B2 * | 9/2007 | Penner | 600/561 |
| 2003/0167079 A1 * | 9/2003 | Birnbaum et al. | 607/60 |
| 2004/0122486 A1 * | 6/2004 | Stahmann et al. | 607/60 |

FOREIGN PATENT DOCUMENTS

| | | |
|---|---|---|
| WO | WO01/41879 A1 | 6/2001 |
| WO | WO 01/42809 | 6/2001 |
| WO | WO 02/39363 | 5/2002 |
| WO | WO 02/067449 | 8/2002 |

* cited by examiner

*Primary Examiner*—Carl H. Layno
*Assistant Examiner*—Tammie K Heller
(74) *Attorney, Agent, or Firm*—Hoffmann & Baron, LLP

(57) ABSTRACT

The invention provides a heart rate monitor, a method and a computer software product. The method determines from the user's electrocardiogram a reference value of a heart rate variable characterizing the heart rate; determines at least one environmental parameter value obtainable from air pressure using air pressure measurement; associates the reference value of the heart rate variable with at least one environmental parameter value; and records in a register at least one environmental parameter value and the reference value of the heart rate variable associated with the at least one environmental parameter value.

20 Claims, 5 Drawing Sheets

HEART RATE MONITOR, METHOD AND COMPUTER SOFTWARE PRODUCT

CROSS-REFERENCE TO RELATED APPLICATION

This application claims priority based on Finnish Patent Application No. 20045392, filed on Oct. 15, 2004, which is incorporated herein by reference.

FIELD OF THE INVENTION

The invention relates to a method for providing heart rate information, to a heart rate monitor and to a computer software product.

BRIEF DESCRIPTION OF THE RELATED ART

As the geographical altitude increases, the atmospheric pressure decreases, which results in reduced air density. As the air density reduces, the oxygen, content per volumetric unit decreases, which produces reactions in human physiological mechanisms, such as blood circulation, respiration and metabolism. At the same time the human aerobic performance declines. Moreover, pressure reduction has particular physiological effects on the human fluid balance, for instance.

Clearly detectable geographical-altitude-related effects on human physiology typically start above 1500 meters, which can be detected as changes in heart rate variables characterizing the heart rate, such as resting heart rate, heart rate during exercise and variations of heart rate. As the altitude increases the resting heart rate and the heart rate during exercise increase as the human body compensates for the oxygen deficit in muscles, whereas the variation of the heart rate and the maximum heart rate generally decrease instead.

In general, the reference values of the heart rate variables are determined at normal pressure. As altitude increases or air density otherwise decreases, the reference value determined at normal pressure does not correspond to pressure conditions, whereby the heart rate monitoring becomes more difficult and the user is not able to monitor his physiological condition on the basis of a variable value characterizing an instantaneous heart rate.

Thus it is useful to examine various manners to provide heart rate information.

SUMMARY OF THE INVENTION

The object of the invention is to provide a heart rate monitor, a method and a computer software product so as to enable the user to take the prevailing pressure conditions into account while he or she monitors his/her physiological condition.

A first aspect of the invention is to provide a user-specific heart rate monitor comprising: characterizing means for determining from the user's electrocardiogram a reference value of a heart rate variable characterizing the heart rate, the reference value of the heart rate variable comprising the user's resting heart rate or a reference value of the user's heart rate variation; determining means for determining at least one environmental parameter value obtainable from the air pressure using air pressure measurement; associating means, connected to the characterizing means and to the determining means, for associating the reference value of the heart rate variable with at least one environmental parameter value; and a register, connected to the associating means, for recording in the register the at least one environmental parameter value and the reference value of the heart rate variable associated with at least one environmental parameter value.

A second aspect of the invention is to provide a user-specific heart rate monitor comprising: characterizing means for determining from the user's electrocardiogram a reference value of a heart rate variable characterizing the heart rate, the reference value of the heart rate variable comprising the user's resting heart rate or a reference value of the user's heart rate variation; determining means for determining one environmental parameter value obtainable from the altitudinal location of the heart rate monitor using altitudinal location measurement; associating means, connected to the characterizing means and to the determining means, for associating the reference value with at least one environmental parameter value; and a register, connected to the associating means, for recording in the register at least one environmental parameter value and a reference value of the heart rate variable associated with the at least one environmental parameter value.

A third aspect of the invention is to provide a user-specific heart rate monitor comprising: characterizing means for determining from the user's electrocardiogram a reference value of a heart rate variable characterizing the heart rate, the reference value of the heart rate variable comprising the user's resting heart rate or a reference value of the user's heart rate variation; determining means for determining an environmental parameter value proportional to air density using measurement of a physical variable proportional to air density; associating means, connected to the characterizing means and to the determining means, for associating the reference value of the heart rate variable with at least one environmental parameter value; and a register, connected the associating means, for recording in the register at least one environmental parameter value and a reference value of the heart rate variable associated with the at least one environmental parameter value.

A fourth aspect of the invention is to provide a method for generating heart rate information, the method comprising: determining from the user's electrocardiogram a reference value of a heart rate variable characterizing the heart rate, the reference value of the heart rate variable comprising the user's resting heart rate or a reference value of the user's heart rate variation; determining at least one environmental parameter value obtainable from air pressure using air pressure measurement; associating the reference value of the heart rate variable with at least one environmental parameter value; and recording in the register at least one environmental parameter value and the reference value of the heart rate variable associated with the at least one environmental parameter value.

A fifth aspect of the invention is to provide a computer software product that includes coded instructions for executing a computer process in a computer of a heart rate monitor, the computer process comprising: determining from the user's electrocardiogram a reference value of a heart rate variable characterizing the heart rate, the reference value of the heart rate variable comprising the user's resting heart rate or a reference value of the user's heart rate variation; determining at least one environmental parameter value obtainable from air pressure using air pressure measurement; associating the reference value with at least one environmental parameter value; and recording in the register at least one environmental parameter value and the reference value of the heart rate variable associated with the at least one environmental parameter value.

The preferred embodiments of the invention are disclosed in the dependent claims.

The invention is based on the idea that by associating a reference value of a heart rate variable, such as resting heart rate, with an environmental parameter value and by recording said values in a register a stored logical data structure will be provided. The logical data structure can be used subsequently to generate heart rate reference information corresponding to prevailing environmental conditions while the heart rate is monitored.

Several advantages are achieved with the heart rate monitor, the method and the computer software product of the invention. One advantage of the invention is to enable calibration of the resting heart rate in the heart rate monitor as a function of pressure, the calibration being available to the user when the determination of the resting heart rate is not possible.

BRIEF DESCRIPTION OF THE DRAWINGS

In the following the invention will be described in greater detail in connection with preferred embodiments with reference to the attached drawings, in which.

DETAILED DESCRIPTION OF THE PREFERRED EMBODIMENTS

Figure 1:
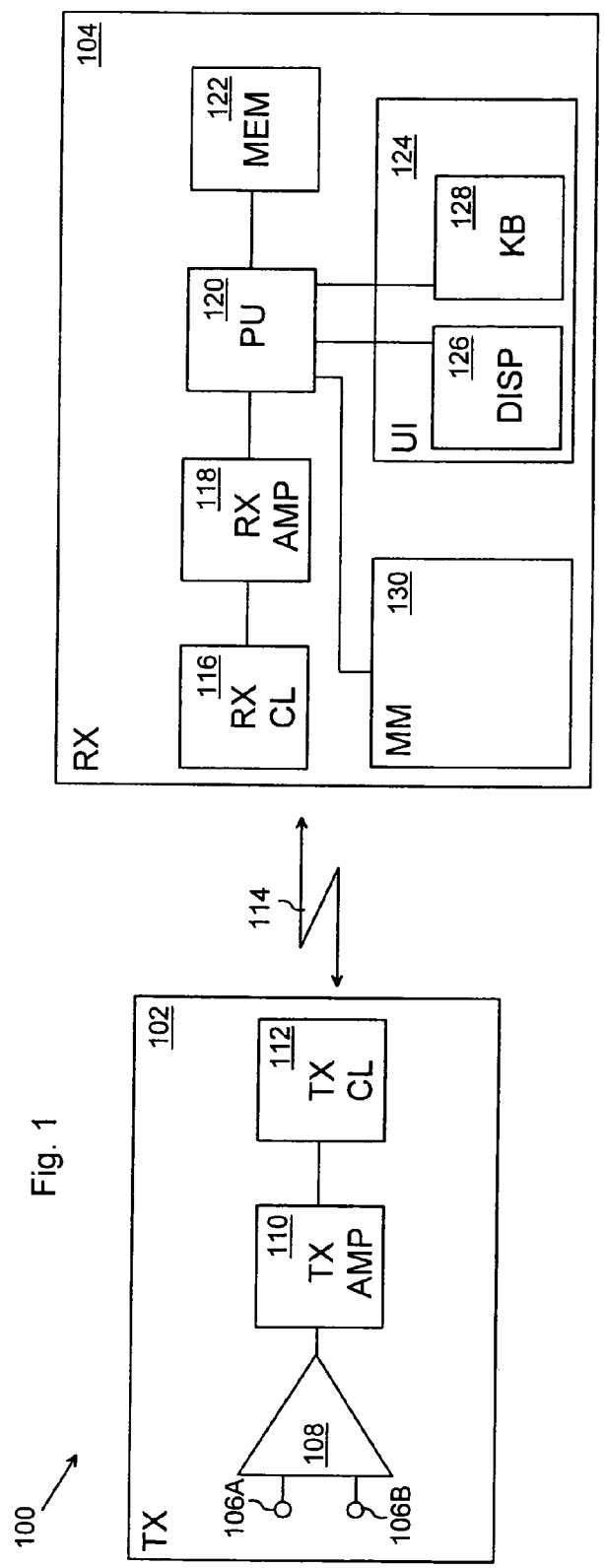
FIG. 1 is an example of the structure of a heart rate monitor.

FIG. 1 shows an example of a structure of a user-specific heart rate monitor 100 based on the use of telemetry. The user-specific heart rate monitor 100 comprises electrodes 106A, 106B, an ECG (ElectroCardio-Gram) preamplifier 108 provided with differential feed poles, a transmitter amplifier (TX AMP) 110, a transmitter coil (TX CL) 112, a receiver coil (RX CL) 116, a receiver amplifier (RX AMP) 118, a processing unit (PU) 120, a memory unit (MEM) 122 and a user interface (UI) 124.

Electrodes 106A, 106B sense the electric potential generated by the electric activity of the heart muscle and produce an ECG signal characterizing the electric activity of the heart muscle. The ECG signal is applied from the electrodes 106A, 106B to the ECG preamplifier 108.

The ECG preamplifier 108 pre-amplifies the ECG signal and feeds the pre-amplified ECG signal to the transmitter amplifier 110. The transmitter amplifier 110 may include a plurality of successive amplification stages, such as an AGC (Automatic Gain Control) amplifier and a power amplifier.

The amplified ECG signal is applied to the transmitter coil 112 that generates an electromagnetic field 114 transferring ECG data. The ECG data may include, for instance, the ECG as such, part of the ECG and/or heart rate timing information. The timing information may include a timing impulse that represents the timing of a predetermined ECG part.

In the given example a magnetic component of the electromagnetic field 114 serves as a transfer mechanism for a wireless connection. The solution presented is not restricted, however, to the use of the magnetic component of the electromagnetic field 114, but the ECG data transfer may use any form of telemetry.

The receiver coil 116 detects the electromagnetic field 114 generated by the transmitter coil 112 and produces an induced electric signal that is applied to the receiver amplifier 118.

The receiver amplifier 118 performs electric signal processing such as filtering and amplifying. In addition, the receiver amplifier may comprise a plurality of successive regulation stages.

The receiver amplifier 118 feeds the electric signal to the processing unit 120 that may perform analog signal modification of the electric signal, such as filtration and analog-to-digital conversions. In addition the processing unit 120 may perform digital processing such as digital filtering, signal shaping, ECG signal detecting, and ECG signal analysing.

In the processing unit 120 it is possible to determine a value for a heart rate variable characterizing the heart rate and/or a reference value for a heart rate variable. The heart rate variable may be a heart rate beat interval, a heart rate frequency, a variation of the heart rate interval and/or a variation of the heart rate frequency. The reference value for the heart rate variable may be a heart rate interval at rest, a heart rate frequency at rest, a reference value of the variation of the heart rate interval and/or a reference value of the variation of the heart rate frequency.

The processing unit 120 can be implemented using analog circuits, ASIC circuits (Application Specific Integrated Circuit), a digital processor, a memory and computer software. The processing unit 120 may be part of the computer in the user-specific heart rate monitor 100.

Part of the data produced by the processing unit 120 can be stored in a memory unit 122 connected to the processing unit 120. In addition the memory unit 122 may include coded instructions for executing a computer process in the processing unit 120.

The user-specific heart rate monitor 100 further comprises a measurement module (MM) 130, which typically measures a value of a physical variable proportional to air density.

In one embodiment the measurement module 130 includes a pressure sensor that measures the ambient air pressure. The pressure sensor may generate a voltage level that is proportional to the pressure and that is converted into numeric format in the processing unit 120, for instance. Small pressure sensors employed in the user-specific heart rate monitor 100 can be implemented, for instance, by piezo resistive silicon components and they represent commercially available technology known per se. Miniature pressure sensors of MS54 series manufactured by Intersema can be given as an example.

In another embodiment the measurement module 130 includes a satellite navigator that determines the location coordinates of the heart rate monitor 100 including altitude data and optionally the time. For instance, the satellite navigator may record the altitude coordinate of the heart rate monitor 100 and optionally other determined coordinates into the processing unit 120. The satellite navigator may operate, for instance, in the GPS system (Global Positioning System), in the GLONASS (Global Navigation Satellite System) system or in another commonly used satellite positioning system. The implementation of the satellite navigator in the user-specific heart rate monitor system applications is technology known per se.

The user interface 124 typically includes a display unit 126 and a display controller. The display unit 126 may include, for instance, LCD components (Liquid Crystal Display). The display unit 126 may display graphically and/or numerically an instantaneous heart rate variable value, a reference value of the heart rate variable and/or measurement information produced by the measurement module 130, such as instantaneous air pressure and/or instantaneous location altitude.

The user interface 124 further includes a keypad 128 by means of which the user may record commands into the user-specific heart rate monitor 100.

The user-specific heart rate monitor 100 is characterized in that the user of the heart rate monitor monitors his or her own condition by means of the heart rate monitor.

The user-specific heart rate monitor 100 shown in FIG. 1 can be divided into a transmitter part 102 and a receiver part 104. The transmitter part 102 typically includes device parts 106A to 112 and it performs the ECG measurement and transmission of the ECG information to the receiver part 104. In some embodiments the transmitter part 102 may include a heart rate detector that detects a predetermined part of the ECG, generates a transmitter burst and/or bit stream representing the timing of the predetermined ECG part and transmits the transmitter burst to the receiver part 104.

The receiver part 104 typically includes device parts 116 to 128 that process the electric signal used in telemetry and the ECG information and provide a user interface. In addition the receiver part 104 typically includes a measurement module 130, but in some embodiments the measurement module 130 may also be located in the transmitter part 102. In that case the information generated by the measurement module 130 can be transmitted telemetrically to the receiver part 104.

Figure 2:
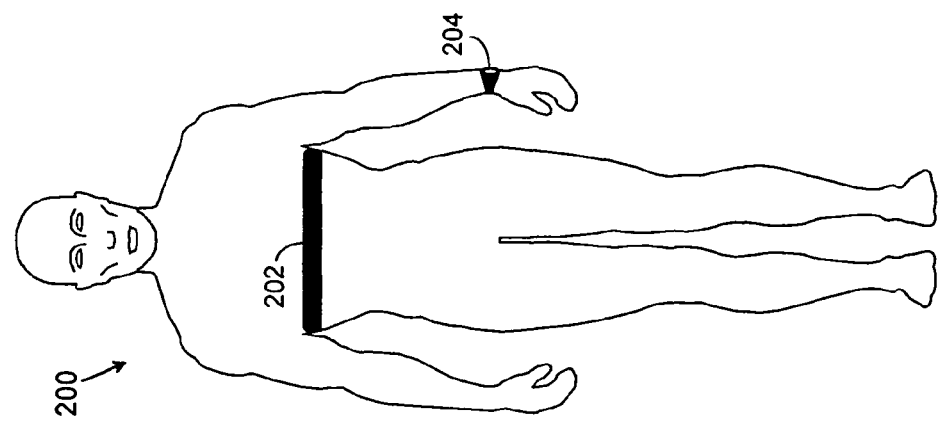
FIG. 2 is an example of a heart rate monitor in connection with a person.

With reference to the embodiment of FIG. 2 the transmitter part 102 is placed in a transmitter belt 202 that is worn around the user's 200 chest. The ECG information is delivered telemetrically from the transmitter belt 202 to the receiver unit 204 that is typically a wrist-worn device. In some embodiments the receiver unit 204 is attachable to bicycle structures such as a handle bar. The placement of the receiver unit 204 is not restricted, however, to the wrist or the handle bar, but it can be placed anywhere with the proviso that a telemetric connection between the transmitter unit 202 and the receiver unit 204 is maintained and that the user is able to use the receiver unit 204.

In one embodiment the transmitter part 102 and the receiver part 104 are integrated in the same heart rate monitor, whereby a user-specific heart rate monitor worn on the wrist or held on the handle bar, for instance, is obtained. In that case some device parts of FIG. 1, such as the coils 112, 116 and the amplifiers 110, 118, are not necessarily needed. In one embodiment the transmitter part 102 and part of the receiver part 104 are integrated in the transmitter belt 202, whereby the transmitter belt 202 may collect ECG data, process the ECG data and determine values of variables characterizing the heart rate. In that case the telemetric data transmission conveys processed data, such as variable values characterizing the heart rate and commands given by the user, from the transmitter belt 202 to the receiver unit 204. In that case the receiver unit 204 may also be telemetrically, optically or galvanically connected to the transmitter belt 202.

Figure 3:
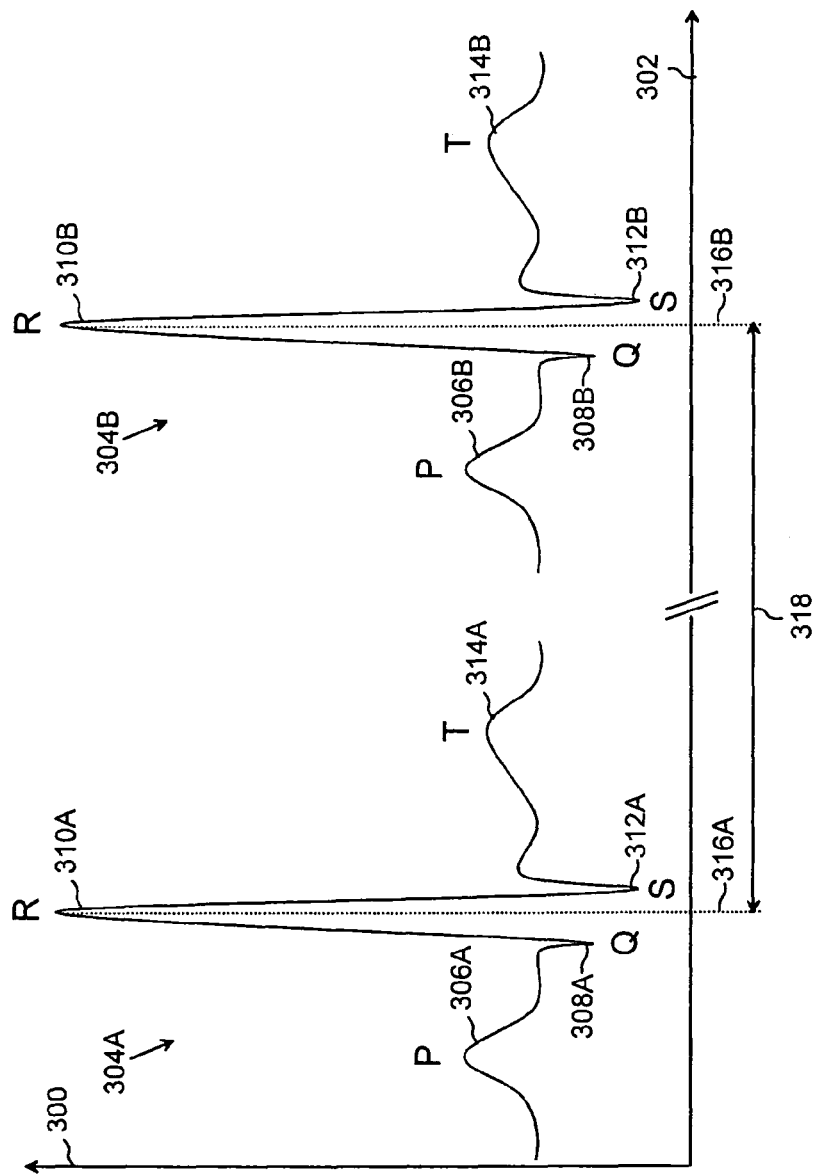
FIG. 3 shows part of an electrocardiogram.

FIG. 3 shows successive ECG pulses 304A, 304B in a time/voltage coordinate system 300, 302.

Each pulse 304A, 304B corresponds to one heartbeat with timing 316A, 316B. The interval between the pulses 304A, 304B is called a heart rate interval 318.

The pulse 304A, 304B has pre-detectable parts, such as P wave 306A, 306B, Q wave 308A, 308B, R wave 310A, 310B, S wave 312A, 312B and/or T wave 314A, 314B, which represent various phases of a heartbeat.

The generation mechanisms of P, Q, R, S and T waves are known per se. The R wave 310A, 310b produces a strong and thus easily detectable structure in the pulse 304A, 304B, so the R wave 310A, 310B is generally used for detecting a QRS complex and for determining the pulse timing 316A, 316B.

The QRS complex can be detected with a pulse detector, for instance. The transmitter part 102 may generate, for instance, a burst corresponding to the timing of each pulse 304A, 304B, the burst being transmitted to the receiver part 104. The receiver part 104 receives the bursts and may determine, for instance, the heart rate interval 318 between the successive bursts. On the basis of the heart rate interval 318 it is possible to generate heart rate variables characterizing the heart rate, such as heart rate frequency, resting heart rate, variation in the heart rate interval and/or a reference value of the variation in the heart rate interval. Determination of the heart rate variables is known per se, and therefore it is not described in greater detail herein. The values of the heart rate variables can be recorded in the memory unit 122 for processing or for subsequent use.

Figure 4B:
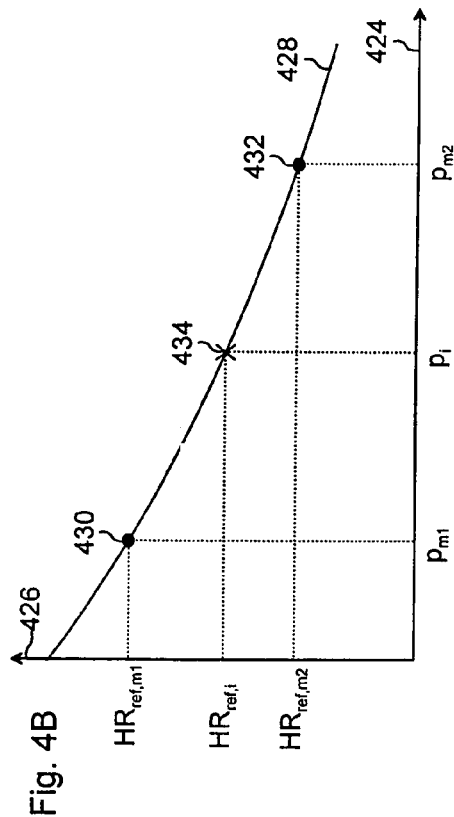
FIG. 4B shows a reference value of a heart rate variable as a function of an environmental parameter value.
Figure 4A:
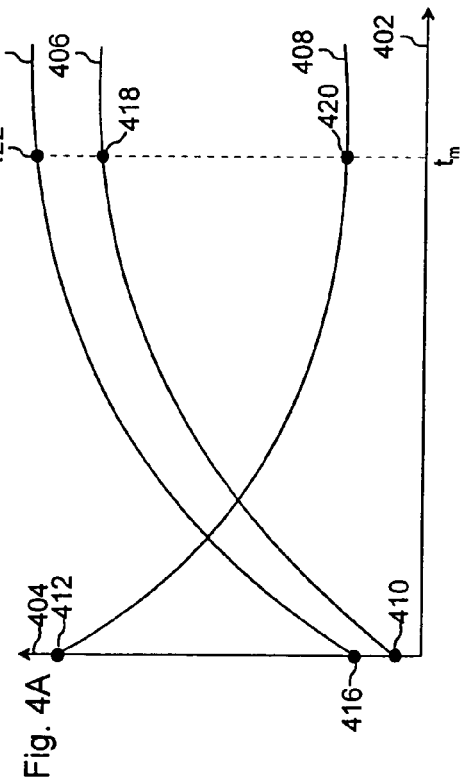
FIG. 4A shows curves including a reference value of a heart rate variable and an environmental parameter value.

FIG. 4A shows an environmental parameter curve 406, 408 representing a value of an environmental parameter and a heart rate variable curve 414 representing a reference value of a heart rate variable. The horizontal axis 402 represents time dimension. It is assumed in FIG. 4A that a change in the environmental parameter causes detectable changes in the value of the heart rate variable characterizing the heart rate and in the reference value of the heart rate variable.

The environmental parameter is typically a parameter characterizing air density in the ambient air of the heart rate monitor, so at the same time the environmental parameter characterizes the oxygen content in a volumetric unit. The environmental parameter may be the pressure prevailing in the vicinity of the heart rate monitor. In one embodiment the environmental parameter is the altitudinal location or the effective altitudinal location of the heart rate monitor. The effective altitudinal location corresponds to a free atmospheric altitude. The effective altitudinal location can be attained under controlled conditions such as in a pressure chamber or in an artificial, low-pressure "alpine hut" (??). The effective altitudinal location can also be linked to the oxygen content of breathing air in a volumetric unit.

As an example of an environmental parameter curve is given an altitude curve 406 that represents the altitudinal location of the heart rate monitor, for instance, in kilometers. Thus the length variable unit such as kilometer appears on the vertical axis 404. The starting point 410 of the altitude curve 406 corresponds, for instance, to the altitude to which the user is acclimatized. The starting point 410 of the altitude curve is the sea level or the altitude of the user's domicile, for instance.

As another example of an environmental parameter is given a pressure curve 408 that is typically a function of the altitudinal location or the effective altitudinal location. Thus the pressure variable unit such as millibar appears on the vertical axis 404. The starting point 412 of the pressure curve 408 is the normal atmospheric pressure (1013 mbar), for instance.

The heart rate variable curve 414 presents the reference value of the heart rate variable as the altitude/pressure conditions change. Thus the heart rate variable unit such as pulse per minute appears on the vertical axis 404. The starting point 416 of the heart rate variable reference value is the resting heart rate at normal atmospheric pressure, for instance.

At the altitude of 2000 meters the heart rate frequency typically increases 10% as compared with the heart rate frequency at the sea level. When reaching the altitude of 4500 meters the heart rate frequency increases about 50% as compared with that at sea level.

The situation in FIG. 4A may represent, for instance, a take-off of an aircraft, whereby the time scale on the horizontal axis is a few minutes. The pressure curve 408 thus corresponds to the pressure inside the aircraft cabin, which does not correspond to the actual altitude of the plane due to the pressurization. Thus, the altitude curve 406 represents the effective altitudinal location. In this case there is no time for acclimatization, and the obtained reference values of the heart rate variable characterize the human's fast physiological response to changes in pressure.

The situation of FIG. 4A may also represent a car drive or a cable car ride in the mountains.

When the environmental parameter varies on a relatively fast time scale, that is, in the order of less than 24 hours, the user's body has not time enough to adapt to the prevailing environmental conditions. Then, the reference value of the heart rate variable does not include the effect of acclimatization on the heart rate variable.

FIG. 4A also shows a sampling point 418, 420 of the environmental parameter curve 406, 408 and a sampling point 422 of the heart rate variable curve 414. The sampling point 418, 420 of the environmental parameter curve 406, 408 is obtained from the determination of a physical variable proportional to air density, such as pressure and/or altitude, at the moment of determination $t_m$. The sampling point 422 of the heart rate variable 414 is obtained from the determination of the reference value of the heart rate variable at the moment of determination $t_m$.

The sampling point 418, 420 of the environmental parameter curve 406, 408 can be determined by measuring a plurality of physical variable values proportional to air density and by calculating the value of the sampling point 418, 420 of the environmental parameter curve 406, 408 corresponding to the moment of determination $t_m$ from the average of the physical variable values proportional to air density. In that case the air pressure is measured, for instance, within a time interval $t_1$ to $t_2$, during which the pressure varies within the pressure range $p_1$ to $p_2$. The pressure value $p_m$ corresponding to the moment of determination $t_m$ will be $p_m=(p_1+p_2)/2$. The pressure value $p_m$ may be as such the environmental parameter value or the altitudinal location $h_m$ can be generated therefrom. In the corresponding manner it is possible to determine the altitudinal location within the range of $h_1$ to $h_2$ by direct measurement, for instance, by means of a satellite navigation system, and to calculate the altitudinal location $h_m$ corresponding to the moment of determination $t_m$ from the expression $h_m=(h_1+h_2)/2$.

The sampling point 422 of the heart rate variable curve 414 can be determined by measuring the heart rate variable within the time interval $t_1$ to $t_2$. The time interval $t_1$ to $t_2$ is typically the time interval used in the determination of the sampling point 418, 420 of the environmental parameter curve 406, 408. From the heart rate variable values determined within the time interval $t_1$ to $t_2$ it is possible to determine a reference value of the heart rate variable, for instance, as an average value. In one embodiment within the time interval $t_1$ to $t_2$ there is measured a heart rate average that corresponds to the resting heart rate.

The environmental parameter value and the reference value of the heart rate variable corresponding to the same moment of determination $t_m$ constitute an associated pair, in which the reference value of the heart rate variable is associated with the environmental parameter value.

When a plurality of sampling points 418, 420 of the environmental parameter curve 406, 408 are measured as the value of the environmental parameter changes the presentation of FIG. 4B is obtained. In FIG. 4B the horizontal axis 424 represents pressure p and the vertical axis 426 represents the reference value $HR_{ref}$ of the heart rate variable. Sampling points 430 and 432, which correspond to coordinates $(p_{m1}, HR_{ref,m1})$ and $(p_{m1}, HR_{ref,m1})$ in said order, are given as examples. Through the coordinates it is possible to form a heart rate variable curve 428.

Figure 5:
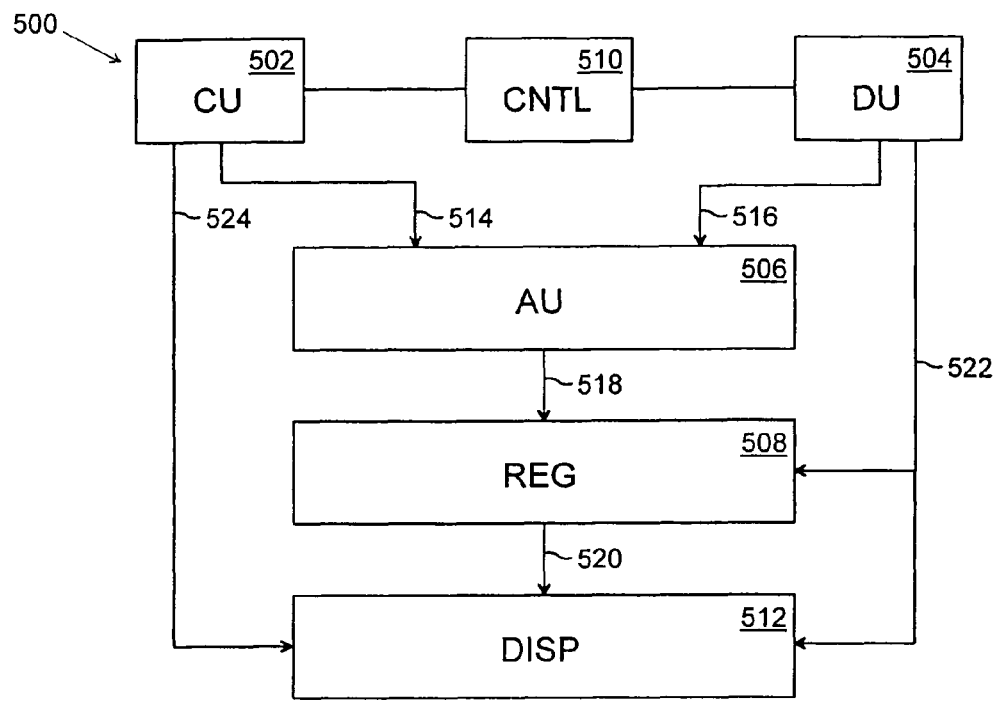
FIG. 5 shows as a flow chart an example of the structure of a heart rate monitor.

FIG. 5 is a block diagram of a heart rate monitor 500. The heart rate monitor 500 comprises a characterization unit (CU) 502 that determines a reference value 514 of a heart rate variable from the user's electrocardiogram. The characterization unit 502 may include, for instance, device parts 116 to 122 of a transmitter part 102 and a receiver part 104 shown in the figure.

The heart rate monitor 500 also comprises a determination unit (DU) 504 that determines an environmental parameter value 516.

The determination unit 504 comprises a measurement module 130 shown in FIG. 1 and optionally parts of a processing unit 120.

In one aspect of the invention the measurement module 130 includes a pressure sensor. In that case the processing unit 120 receives pressure information generated by the pressure sensor and generates from the pressure information an air pressure and an altitudinal location.

In a second aspect of the invention the measurement module 130 includes means, such as a satellite navigator, for measuring the altitudinal location. In that case the processing unit 120 receives from the measurement module 130 location information and generates from the location information an altitudinal location or an air pressure.

It is possible to use the air pressure and/or the altitudinal location as the environmental parameter value.

Conversions between the air pressure and the altitudinal location can be carried out in the processing unit 120 using the digital processor and the computer program of the processing unit 120.

The characterization unit 502 feeds the reference value 514 of the heart rate variable to an association unit (AU) 506. The determination unit 504 feeds the environmental parameter value 516 to the association unit 506.

The association unit 506 provides a logical link between the environmental parameter value 516 and the reference value 514 of the heart rate variable associated with the environmental parameter value 516. The logical link may be based, for instance, on indexing, by which the reference value 514 of the heart rate variable associated with the environmental parameter value 516 is indexed.

The association unit 506 can be implemented, for instance, in the processing unit 120 by means of a digital processor and a computer program.

The association unit 506 records a data element 518 comprised by the environmental parameter value 516 and the reference value 514 of the heart rate variable associated with the environmental parameter value 516 into a register (REG) 508. Thus the register 508 includes the environmental parameter 516 value and the reference value 514 of the heart rate variable associated with the environmental parameter value 516. The register 508 can be implemented, for instance, in the memory unit 122 of FIG. 1. In addition the processing unit 120 may perform some register 508 functions such as indications to the memory of the register and restoration of data stored in the indicated memory locations.

In one embodiment the determination unit 504 determines a plurality of environmental parameter values 516 of different magnitudes and the characterization unit 502 determines a plurality of reference values 514 of the heart rate variable, for instance, by performing determinations of the sampling points 418, 420, 422 of FIG. 4A for a plurality of successive determination moments $t_m$. Thus is obtained, for instance, the sampling points 430, 432 of the heart rate variable curve 428 shown in FIG. 4B, which sampling points characterize the reference point of the heart rate variable as a function of air pressure.

The association unit 506 associates the reference values of the heart rate variable with the values of the environmental parameter such that each reference value 514 of the heart rate variable is associated with the environmental parameter value 516 determined at the moment of determination $t_m$ of the heart rate variable reference value 514.

The register 508 may comprise a logical data structure, such as a table, into which the environmental parameter values 516 and the reference values 514 of the heart rate variable associated therewith are recorded.

In one embodiment the heart rate monitor 500 comprises a controller 510 connected to the determination unit 504 and to the characterization unit 502. In one embodiment the controller starts the determination of the reference values 514 of the heart rate variable on the basis of the environmental parameter values 516. The controller 510 may include an algorithm that monitors, for instance, the environmental parameter values 516 as a function of time. In one embodiment the determination of the reference values 514 of the heart rate variable is started when a predetermined change rate is detected in the environmental parameter value 516. The predetermined change rate is typically defined to be so high that the user will not be able to attain by himself such a big change in pressure and/or effective altitude by walking or cycling, for instance. The selection of the predetermined change rate permits one to detect, for instance, that the user is aboard an aeroplane or in another environment that enables a fast change in pressure and/or effective altitude, whereby the effect of acclimatization on the reference value of the heart rate variable is minimized. The predetermined change rate of the environmental parameter may be in the order of 100 m/min or 10 mbar/min, for instance, but the presented solution is not restricted to those figures, however.

In one embodiment the controller 510 ends the determination of the reference values of the heart rate variable and the determination of the environmental parameter values 516 on the basis of the environmental parameter values. The controller may monitor and end the determination of the environmental parameter values and the reference values of the heart rate variable when the environmental parameter value reaches a threshold value. The threshold value may be a predetermined resting heart rate level or it may be a value generated from previous measurements of the environmental parameter values 516. Thus, for instance, as the pressure in the aircraft cabin is balanced, the controller detects the balancing of the pressure and ends the determination of the resting heart rate automatically.

The above-described determination, association and recording of the environmental parameter values 516 and the reference values 514 of the heart rate variables associated therewith enable calibration of the reference value of the heart rate variable with respect to the environmental parameter value. The logical data structure included in the register 508 and the environmental parameter values recorded therein and the reference values of the heart rate variable associated therewith can be utilized in a variety of ways.

In one embodiment the determination unit 504 determines an instantaneous value 522 of an environmental parameter while the user is experiencing a strain for instance in the mountains. In that case the determination of the actual resting heart rate may be difficult due to a pre-measurement strain, possibly of long duration, and to the acclimatization.

The determination unit 504 records the instantaneous value 522 of the environmental parameter into the register 508.

The register 508 restores the reference value 520 of the heart rate variable to be associated with the instantaneous value 522 of the environmental parameter by using the environmental parameter values and the reference value of the heart rate variable associated with each environmental parameter value recorded in the register 508.

The register 508 does not necessarily include in advance the exact instantaneous value 522 of the environmental parameter and the reference value 520 of the heart rate variable to be associated therewith. So, the register 508 may determine the reference value 520 of the heart rate variable to be associated with the instantaneous value 522 of the environmental parameter, for instance, by using interpolation or optionally extrapolation. This can be performed, for instance, by forming a heart rate variable curve 428 as shown in FIG. 4B and by searching a point 434 therein that corresponds to instantaneous pressure $p_i$ and the reference value $HR_{ref,i}$ of the heart rate variable corresponding to the instantaneous pressure.

In one embodiment the instantaneous value 522 of the environmental parameter is applied to a display unit (DISP) 512 that is configured to display the instantaneous value 522 of the environmental parameter and the reference value 520 of the heart rate variable to be associated with the instantaneous value 522 of the environmental parameter restored by the register. In that case the user may monitor the prevailing ambient pressure and the value of his resting heart rate corresponding to the pressure.

In one embodiment the characterization unit 502 determines an instantaneous value 524 of the heart rate variable characterizing the heart rate, such as the heart rate during exercise. The instantaneous value 524 of the heart rate variable can be fed into the display unit 512 and displayed in relation to the reference value 520 of the heart rate variable associated with the instantaneous value 522 of the environmental parameter. In that case the user may compare the instantaneous heart rate during exercise to the reference value of the heart rate corresponding to the prevailing pressure and/or altitude and adapt his physical strain in view of the prevailing pressure conditions.

The display unit 512 may be, for instance, a display unit 126 as shown in FIG. 1.

Figure 6:
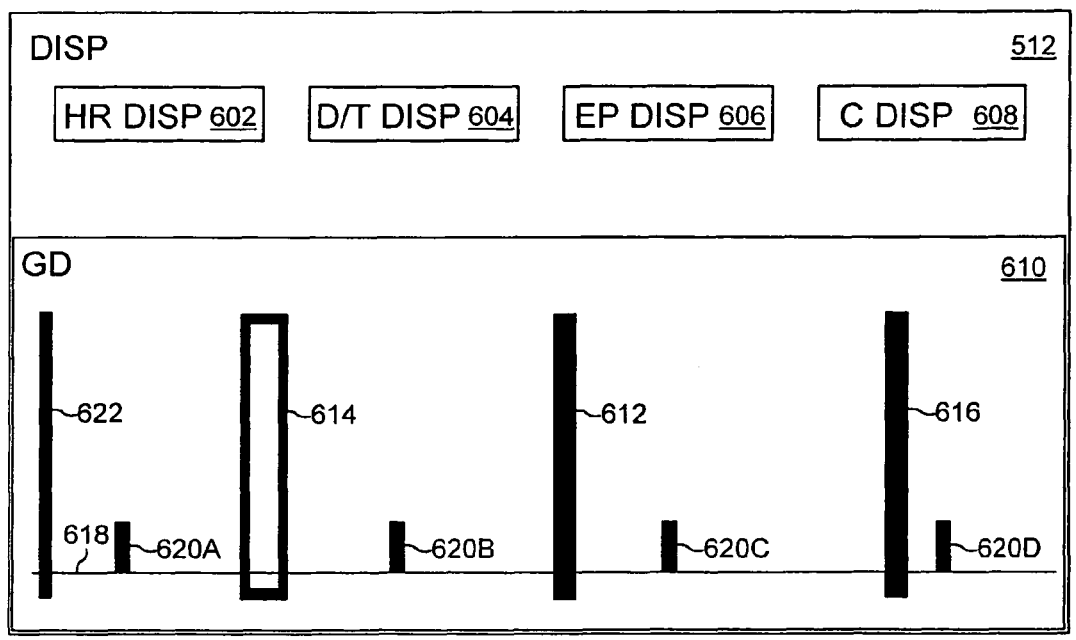
FIG. 6 is an example of a display unit of the heart rate monitor.

With reference to FIG. 6 the display unit may comprise a heart rate display segment (HR DISP) 602, a time display segment (D/T DISP) 604, an environmental parameter display segment (EP DISP) 606 and a control segment (C DISP) 608.

The heart rate display segment 602 typically shows an instantaneous numerical value of a heart rate variable, such as the instantaneous heart rate frequency or the instantaneous heart rate variation.

The time display segment 604 displays numerically a time variable such as the date, the time and/or a time variable relating to timing.

The environmental parameter display segment 606 displays numerically an instantaneous value 522 of an environmental parameter, such as pressure or altitude.

The control segment 608 typically displays menu elements and parameter values representing the operation of the heart rate monitor.

The display unit 512 may also include a graphic display (GD) 610 for graphical representation of the heart rate information and the environmental parameter information. The graphic display 610 may include a horizontal axis 618 and a scale 620A, 620B, 620C, 620D.

In one embodiment the display unit 610 displays the reference value 520 of the heart rate variable associated with the instantaneous value of the environmental parameter with a reference value indicator 614, the horizontal position of which indicates the resting heart rate corresponding to the prevailing air pressure. In addition the display unit 610 may display an instantaneous value 524 of the heart rate variable with a heart rate variable indicator 612, the horizontal position of which depends on the instantaneous value 524 of the heart rate variable. The user may thus monitor the instantaneous value of the heart rate in relation to the resting heart rate corresponding to the prevailing air pressure by comparing the position of the heart rate variable indicator 612 to that of the reference value indicator 614.

The graphic display 610 may also include a maximum value indicator 616 that indicates a maximum value of a heart rate variable, such as the maximum heart rate or any other value of a variable characterizing the upper limit of the heart rate variable. The user may compare the position of the heart rate variable indicator 612 to that of the maximum value indicator 616 and adapt the strain suitably.

The graphic display 610 may also include a second reference value indicator 622. The second reference value indicator 622 may indicate the reference value of the heart rate variable stored in the register 510 in other than prevailing circumstances. In one embodiment the second reference value indicator 622 indicates the user's acclimatized resting heart rate. The acclimatized resting heart rate is a resting heart rate that is attained when the user has adapted to the ambient conditions. The acclimatized resting heart rate may be, for instance, the resting heart rate in the atmospheric normal pressure.

Figure 7:
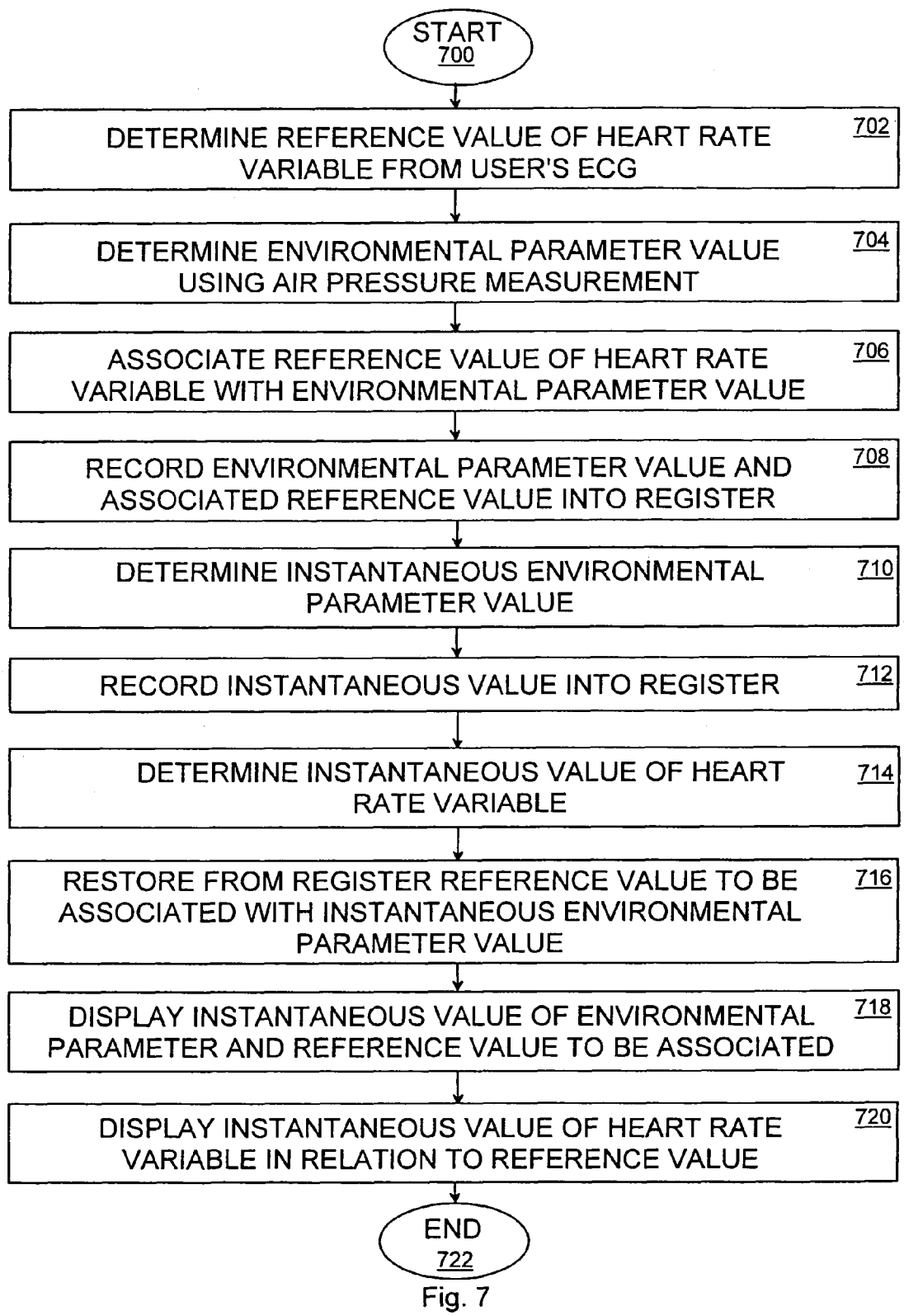
FIG. 7 shows a first example of a method in accordance with an embodiment.
Figure 8:
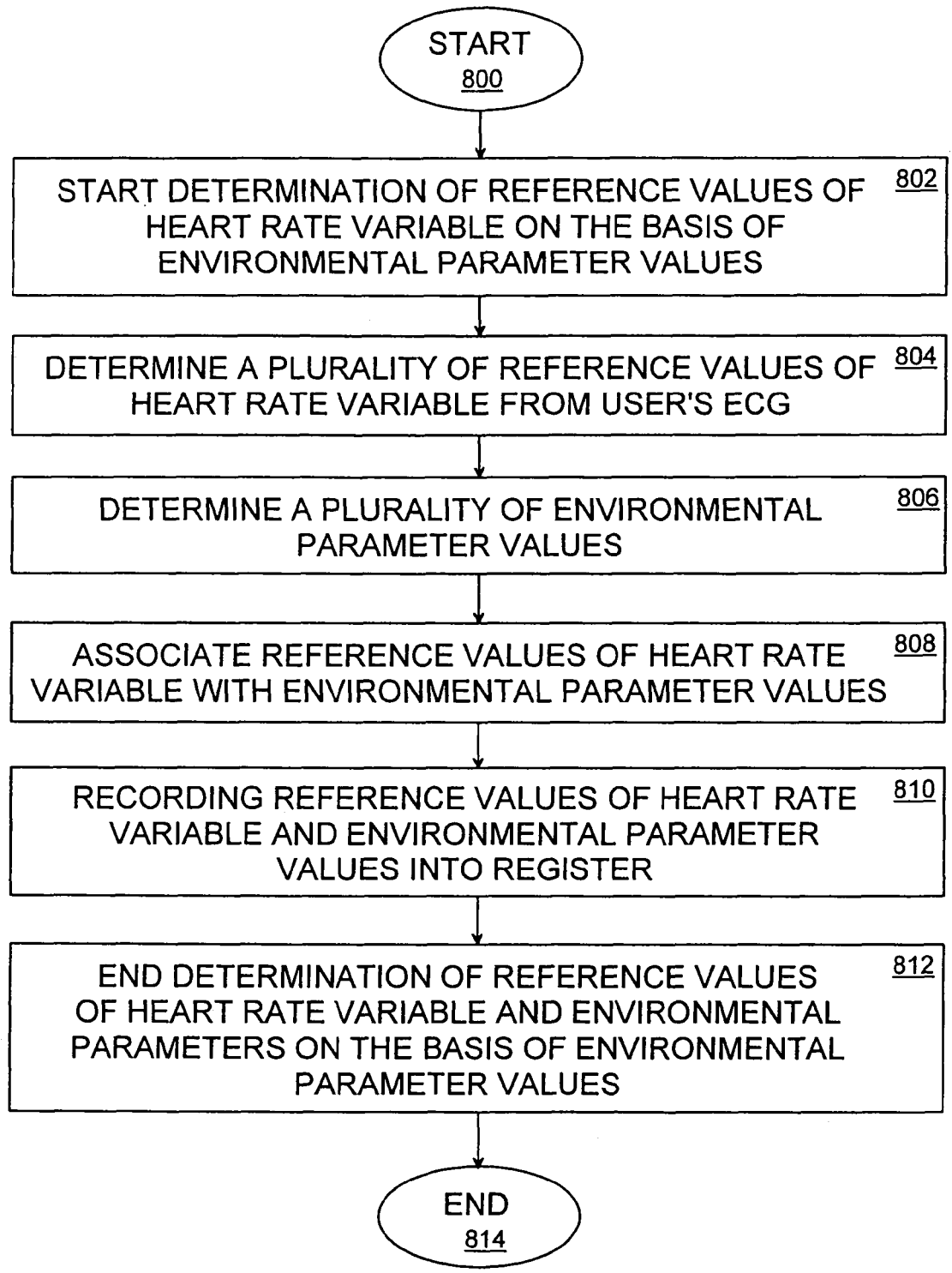
FIG. 8 shows a second example of a method in accordance with an embodiment.

FIGS. 7 and 8 show methods in accordance with the presented solution.

In FIG. 7 the method starts at 700.

At 702 a reference value 514 of a heart rate variable characterizing the heart rate is determined from the user's electrocardiogram.

At 704 at least one value 516 of an environmental parameter obtainable from the air pressure is determined using air pressure measurement.

At 706 the reference value 514 of the heart rate variable is associated with at least one environmental parameter value 516.

At 708 at least one value 516 of the environmental parameter and the reference value 514 of the heart rate variable associated with the at least one environmental parameter value are recorded in the register.

At 710 an instantaneous value 522 of the environmental parameter is determined.

At 712 an instantaneous value 522 of the environmental parameter is recorded in the register 510.

At 714 an instantaneous value 524 of a heart rate variable characterizing an instantaneous heart rate is determined from the user's electrocardiogram.

At 716 the reference value 522 of the heart rate variable to be associated with the instantaneous value 522 of the environmental parameter is restored from the register 510 using the environmental parameter values recorded in the register 510 and the reference value 514 of the heart rate variable associated with each environmental parameter value.

At 718 the instantaneous value 522 of the environmental parameter and the reference value of the heart rate variable to be associated with the instantaneous environmental parameter value 522 are displayed.

At 720 there are displayed the reference value 520 of the heart rate variable to be associated with the instantaneous environmental parameter value 522 and the reference value 524 of the heart rate variable in relation to the reference value 520 of the heart rate variable to be associated with the instantaneous environmental parameter value 522.

The method ends at 722.

In FIG. 8 the method starts at 800.

At 802 the determination of reference values 514 of a heart rate variable is started on the basis of environmental parameter values 516.

At 804 a plurality of reference values of the heart rate variable characterizing the heart rate are determined from the user's electrocardiogram.

At 806 a plurality of environmental parameter values 516 of different magnitudes are determined.

At 808 the reference values 514 of the heart rate variable are associated with the environmental parameter values 516 such that each reference value 514 of the heart rate variable is associated with the environmental parameter value 516 determined at the determination moment of the reference value 514 of the heart rate variable.

At 810 each environmental parameter value 516 and a reference value 514 of the heart rate variable associated with the environmental parameter value 516 are recorded in the register 510.

At 812 the determination of the reference values 514 of the heart rate variable and the determination of the environmental parameter values 516 on the basis of the environmental parameter values are finished.

At 814 the method ends.

One aspect of the invention is a computer software product that includes coded instructions for executing a computer process in the computer of the heart rate monitor. The embodiments of the computer process appear in FIGS. 7 and 8.

The computer software product can be stored on a distribution medium, such as a magnetic and/or optical storing medium, a hard disk or another means suitable for data storage and/or transfer. In addition the computer software product can be transferred using a computer-readable signal, such as a telecommunications signal.

Even though the invention is described above with reference to the accompanying drawings, it is obvious that the invention is not restricted thereto but it may be modified in a variety of ways within the scope of the attached claims.

What is claimed is:

1. A user-specific heart rate monitor comprising:
 a characterizing unit to determine from a user's electrocardiogram a reference value of a heart rate variable characterizing the heart rate;
 a determining unit to determine at least one environmental parameter value proportional to air density using measurement of a physical variable proportional to air density;
 an associating unit, connected to the characterizing unit and to the determining unit, to associate the reference value of the heart rate variable with the at least one environmental parameter value, the at least one environmental parameter value associated with the reference value of the heart rate variable; and
 a register, connected to the associating unit, to record in the register the at least one environmental parameter value and the reference value of the heart rate variable associated with the at least one environmental parameter value, the register determining and outputting the reference value of the heart rate variable to be associated with an instantaneous value of the at least one environmental parameter value by using the instantaneous value of the at least one environmental parameter value, the at least one environmental parameter value in the register, and the reference value of the heart rate variable associated with the at least one environmental parameter value in the register.

2. The heart rate monitor of claim 1, wherein the characterizing unit is arranged to determine from the user's electrocardiogram a plurality of reference values of the heart rate variable characterizing the heart rate;
wherein the determining unit determines a plurality of environmental parameter values of different magnitudes;
wherein the associating unit associates the reference values of the heart rate variable with the environmental parameter values such that each reference value of the heart rate variable is associated with the environmental parameter value determined at a moment the reference value of the heart rate variable is determined; and
wherein the register records each environmental parameter value and the reference value of the heart rate variable associated with each environmental parameter value.

3. The heart rate monitor of claim 2, the heart rate monitor further comprising staffing means connected to the characterizing unit and to the determining unit, the starting means starting the determination of the reference values of the heart rate variable on the basis of the environmental parameter values.

4. The heart rate monitor of claim 2, the heart rate monitor further comprising an ending unit connected to the characterizing unit and to the determining unit, the ending unit ending the determination of the reference values of the heart rate variable and the determination of the environmental parameter values on the basis of the environmental parameter values.

5. The heart rate monitor of claim 1, wherein the determining unit is configured to determine an instantaneous environmental parameter value;
wherein the determining unit records the instantaneous environmental parameter value into the register;
wherein the register determines and outputs the reference value of the heart rate variable to be associated with the instantaneous environmental parameter value by using the instantaneous environmental parameter value, the environmental parameter values, and the reference value of the heart rate variable associated with each environmental parameter value recorded in the register, the heart rate monitor further comprising an instantaneous environmental parameter value display unit to display the instantaneous environmental parameter value and the reference value of the heart rate variable to be associated with the instantaneous environmental parameter value.

6. The heart rate monitor of claim 1, wherein the characterizing unit is arranged to determine from the user's electrocardiogram an instantaneous value of the heart rate variable characterizing an instantaneous heart rate;
wherein the determining unit determines an instantaneous environmental parameter value;
wherein the determining unit records the instantaneous environmental parameter value into the register;
wherein the register determines and outputs the reference value of the heart rate variable to be associated with the instantaneous environmental parameter value by using the instantaneous environmental parameter value, the environmental parameter values, and the reference value of the heart rate variable associated with each environmental parameter value recorded in the register, the heart rate monitor further comprising a reference value display unit to display the reference value of the heart rate variable to be associated with the instantaneous environmental parameter value and the instantaneous value of the heart rate variable in relation to the reference value of the heart rate variable associated with the instantaneous environmental parameter value.

7. The heart rate monitor of claim 1, wherein the reference value of the heart rate variable is at least one of the following: the user's resting heart rate, the reference value of the user's heart rate variation.

8. The heart rate monitor of claim 1, wherein the environmental parameter is at least one of the following: the measured air pressure, the altitudinal location of the heart rate monitor.

9. A method of providing heart rate information, comprising:
determining from a user's electrocardiogram a reference value of a heart rate variable characterizing the heart rate;
determining at least one environmental parameter value proportional to air density using measurement of a physical variable proportional to air density;
associating the reference value of the heart rate variable with the at least one environmental parameter value, the at least one environmental parameter value associated with the reference value of the heart rate variable;
recording in a register the at least one environmental parameter value and the reference value of the heart rate variable associated with the at least one environmental parameter value; and
determining and outputting by the register the reference value of the heart rate variable to be associated with an instantaneous value of the at least one environmental parameter value by using the instantaneous value of the at least one environmental parameter value, the at least one environmental parameter value in the register, and the reference value of the heart rate variable associated with the at least one environmental parameter value in the register.

10. The method of claim 9, further comprising:
determining from the user's electrocardiogram a plurality of reference values of the heart rate variable characterizing the heart rate;
determining a plurality of environmental parameter values of different magnitudes;
associating the reference values of the heart rate variable with the environmental parameter values such that each reference value of the heart rate variable is associated with the environmental parameter value determined at a determination moment of the reference value of the heart rate variable; and
recording in the register each environmental parameter value and the reference value of the heart rate variable associated with each environmental parameter.

11. The method of claim 10, further comprising staffing a determination of the reference values of the heart rate variable on the basis of the environmental parameter values.

12. The method of claim 10, further comprising ending a determination of the reference values of the heart rate variable and the determination of the environmental parameter values on the basis of the environmental parameter values.

13. The method of claim 9, further comprising:
determining an instantaneous value of an environmental parameter;
recording the instantaneous value of the environmental parameter into the register;

determining and outputting from the register the reference value of the heart rate variable to be associated with the instantaneous environmental parameter value using fin instantaneous environmental parameter value, the environmental parameter values, and the reference value of the heart rate variable associated with each environmental parameter value recorded in the register; and displaying the instantaneous environmental parameter value and the reference value of the heart rate variable to be associated with each environmental parameter value.

14. The method of claim 9, further comprising:

determining an instantaneous value of an environmental parameter;

recording the instantaneous value of the environmental parameter into the register;

determining from the user's electrocardiogram an instantaneous value of the heart rate variable characterizing the heart rate;

determining and outputting from the register the reference value of the heart rate variable to be associated with the instantaneous environmental parameter value using the instantaneous environmental parameter value, the environmental parameter values, and the reference value of the heart rate variable associated with each environmental parameter value recorded in the register; and displaying the reference value of the heart rate variable to be associated with the instantaneous environmental parameter value and the instantaneous value of the heart rate variable in relation to the reference value of the heart rate variable to be associated with the instantaneous environmental parameter value.

15. A tangible computer readable software carrier that includes computer instructions thereon, which when executed by a computer of a heart rate monitor provide heart rate information by:

determining from a user's electrocardiogram a reference value of a heart rate variable characterizing the heart rate;

determining at least one environmental parameter value proportional to air density using a measurement of a physical variable proportional to air density;

associating the reference value of the heart rate variable with the at least one environmental parameter value, the at least one environmental parameter value associated with the reference value of the heart rate variable;

recording in a register at least one environmental parameter value and the reference value of the heart rate variable associated with the at least one environmental parameter value; and determining and outputting by the register the reference value of the heart rate variable to be associated with an instantaneous value of the at least one environmental parameter value by using the instantaneous value of the at least one environmental parameter value, the at least one environmental parameter value in the register, and the reference value of the heart rate variable associated with the at least one environmental parameter value in the register.

16. The tangible computer readable software carrier of claim 15, that further includes computer instructions thereon, which when executed by the computer of the heart rate monitor provide heart rate information by:

determining from the user's electrocardiogram a plurality of reference values of the heart rate variable characterizing the heart rate;

determining a plurality of environmental parameter values of different magnitudes;

associating the reference values of the heart rate variable with the environmental parameter values such that each reference value of the heart rate variable is associated with the environmental parameter value determined at a determination moment of the reference value of the heart rate variable; and recording in the register each environmental parameter value and the reference value of the heart rate variable associated with each environmental parameter.

17. The tangible computer readable software carrier of claim 16 that further includes computer instructions thereon, which when executed by the computer of the heart rate monitor provide heart rate information by starting a determination of the reference values of the heart rate variable on the basis of the environmental parameter values.

18. The tangible computer readable software carrier of claim 16 that further includes computer instructions thereon, which when executed by the computer of the heart rate monitor provide heart rate information by ending a determination of the reference values of the heart rate variable and the determination of the environmental parameter values on the basis of the environmental parameter values.

19. The tangible computer readable software carrier of claim 15 that further includes computer instructions thereon, which when executed by the computer of the heart rate monitor provide heart rate information by determining an instantaneous value of an environmental parameter; recording the instantaneous value of the environmental parameter into the register;

determining and outputting from the register the reference value of the heart rate variable to be associated with the instantaneous environmental parameter value using the instantaneous environmental parameter value, the environmental parameter values, and the reference value of the heart rate variable associated with each environmental parameter value recorded in the register; and displaying the instantaneous environmental parameter value and the reference value of the heart rate variable to be associated with each environmental parameter value.

20. The tangible computer readable software carrier of claim 15 that further includes computer instructions thereon, which when executed by the computer of the heart rate monitor provide heart rate information by determining an instantaneous value of an environmental parameter;

recording the instantaneous value of the environmental parameter into the register;

determining from the user's electrocardiogram an instantaneous value of the heart rate variable characterizing the heart rate;

determining and outputting from the register the reference value of the heart rate variable to be associated with the instantaneous environmental parameter value using the instantaneous environmental parameter value, the environmental parameter values, and the reference value of the heart rate variable associated with each environmental parameter value recorded in the register; and displaying the reference value of the heart rate variable to be associated with the instantaneous environmental parameter value and the instantaneous value of the heart rate variable in relation to the reference value of the heart rate variable to be associated with the instantaneous environmental parameter value.

* * * * *